US00PP12705P2

(12) United States Plant Patent
Covington

(10) Patent No.: US PP12,705 P2
(45) Date of Patent: Jun. 18, 2002

(54) LANTANA PLANT NAMED 'SAMSON'

(75) Inventor: James S. Covington, Clinton, MS (US)

(73) Assignee: Clinton Nursery, Inc., Clinton, MS (US)

( * ) Notice: Subject to any disclaimer, the term of this patent is extended or adjusted under 35 U.S.C. 154(b) by 0 days.

(21) Appl. No.: 09/822,005

(22) Filed: Mar. 31, 2001

(51) Int. Cl.[7] ..... A01H 5/00

(52) U.S. Cl. ..... Plt./227
(58) Field of Search ..... Plt./227

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Lantana plant named 'Samson', characterized by its upright, mounded and outwardly spreading plant habit; freely branching habit; freely and consistent flowering habit; golden yellow and orange-colored flowers; and excellent garden performance.

1 Drawing Sheet

BACKGROUND OF THE INVENTION

The present Invention relates to a new and distinct cultivar of Lantana plant, botanically known as *Lantana camara,* and hereinafter referred to by the cultivar name 'Samson'.

The new Lantana was discovered by the Inventor in Clinton, Miss., as a naturally-occurring branch mutation of an unidentified selection of *Lantana camara.*

Asexual reproduction of the new cultivar by terminal cuttings taken in Clinton, Miss., since the summer of 1999, has shown that the unique features of this new Lantana are stable and reproduced true to type in successive generations.

SUMMARY OF THE INVENTION

Plants of the cultivar 'Samson' have not been observed under all possible environmental conditions. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Samson'. These characteristics in combination distinguish 'Samson' as a new and distinct cultivar:

1. Upright, mounded and outwardly spreading plant habit.
2. Freely branching.
3. Freely and consistently flowering.
4. Golden yellow and orange-colored flowers.
5. Excellent garden performance.

Plants of the new Lantana differ from plants of the parent selection primarily in flower color as plants of the parent selection have yellow and red colored inflorescences.

Plants of the new Lantana can be compared to plants of the cultivar 'Sonrise', disclosed in U.S. Plant Pat. No. 10,856. However, in side-by-side comparisons conducted by the Inventor in Clinton, Miss., plants of the new Lantana differ from plants of the cultivar 'Sonrise' in the following characteristics:

1. Plants of the new Lantana are more freely and more consistently flowering than plants of the cultivar 'Sonrise'.

2. Plants of the new Lantana and the cultivar 'Sonrise' differ in flower coloration.

Plants of the new Lantana can also be compared to plants of the cultivar 'Radiation', not patented, which is similar in flower color to plants of the new Lantana. However, in side-by-side comparisons conducted by the Inventor in Clinton, Miss., plants of the new Lantana differ from plants of the cultivar 'Radiation' in the following characteristics:

1. Plants of the new Lantana are more upright, uniform, mounded and vigorous than plants of the cultivar 'Radiation'.

2. Plants of the new Lantana are more freely and more consistently flowering than plants of the cultivar 'Radiation'.

3. Plants of the new Lantana are more hardy than plants of the cultivar 'Radiation'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Latana.

The photograph at the top of the sheet comprises a side perspective view of a typical plant of 'Samson'.

The photograph at the bottom of the sheet comprises a close-up view of typical flowers and leaves of 'Samson'.

DETAILED BOTANICAL DESCRIPTION

In the following description, color references are made to The Royal Horticultural Society Colour Chart except where general terms of ordinary dictionary significance are used. Plants grown in 1.5-gallon containers were used for the photographs and following description. Plants were grown under outdoor conditions in Clinton, Miss. and Keller, Tex. during the spring and summer and were about 4 to 6 months old.

Botanical classification: *Lantana camara* cultivar 'Samson'.
Parentage: Naturally-occurring branch mutation of an unidentified selection of *Lantana camara,* not patented.

Propagation:

*Type cutting.*—Terminal cuttings.

*Time to initiate roots, summer.*—About 7 to 10 days at 32° C.

*Time to initiate roots, winter.*—About 10 to 14 days at 18° C.

*Time to develop roots, summer.*—About 14 to 28 days at 32° C.

*Time to develop roots, winter.*—About 20 to 40 days at 18° C.

*Root description.*—Numerous, fibrous and well-branched.

Plant description:

*Form.*—Perennial flowering plant; subshrub; initially upright, then outwardly spreading; mounded; relatively compact. Freely branching; lateral branches potentially forming at every node; pinching enhances lateral branch development.

*Usage.*—Appropriate for hanging baskets, window boxes, patio containers and landscape applications.

*Plant height.*—About 32 cm.

*Plant diameter.*—About 47 cm.

*Vigor.*—Moderately vigorous.

*Lateral branches.*—Length: About 25 cm. Diameter: About 2 mm. Internode length: About 3.3 cm. Aspect: Initially upright, then bending about 45° from upright. Strength: Flexible, but strong. Texture: Pubescent; fine white hairs; coarse. Color: Young: 144A. Woody: Close to 199B.

*Foliage description.*—Leaves simple, generally symmetrical and long-persisting; opposite. Length: About 4.8 cm. Width: About 3.9 cm. Shape: Ovate. Apex: Acute. Base: Obtuse to truncate. Margin: Crenate to serrate. Texture: Rough, coarse; pubescence on both surfaces; rugose. Fragrance: Pungent, herb-like; pleasant. Color: Young foliage, upper surface: 146A. Young foliage, lower surface: 146B. Mature foliage, upper surface: 147A. Mature foliage, lower surface: 147B. Veins, upper surface: 147A. Veins, lower surface: 147B. Petiole length: About 7.5 mm. Petiole diameter: About 1.5 mm. Petiole color: 147A to 147B.

Flower description:

*Flower type and habit.*—Small salverform flowers arranged in axillary umbels; flowers face mostly upward or outward. Flowers self-cleaning. Very freely flowering with potentially two inflorescences per node; typically about 32 flowers per umbel.

*Natural flowering season.*—Spring until frost in the autumn; flowering continuous and consistent.

*Flower longevity on the plant.*—About one week.

*Fragrance.*—Faint, sweet, pleasant.

*Inflorescence diameter.*—About 4.7 cm.

*Inflorescence height.*—About 2.4 cm.

*Flowers.*—Appearance: Flared trumpet, corolla fused, four-parted; flowers roughly rectangular in shape. Diameter: About 1.3 cm by 1 cm. Corolla tube length: About 1.1 cm.

*Flower buds* (*just before showing color*).—Length: About 4 mm. Diameter: About 2.75 mm. Shape: Oblong. Color: 146A to 146B.

*Corolla.*—Arrangement/appearance: Single whorl of four petals, fused into flared trumpet. Petal length from throat: Upper petal, about 6.5 mm; lower and lateral petals, about 4.5 mm. Petal width: Upper petal, about 8 mm; lower petal, about 7 mm; lateral petals, about 6 mm. Petal shape: Upper and lower petals, somewhat spatulate; lateral petals, mostly orbicular. Petal apex: Rounded. Petal margin: Entire. Petal texture: Smooth, satiny; throat, whiskered. Color: Petal, upper surface, when opening: Close to 14A. Petal, lower surface, when opening: Close to 14A to 14B. Petal, upper surface, fully opened: Close to 34A, becoming darker, close to 42A, with subsequent development; throat, close to 14A. Petal, lower surface and tube, fully opened: Close to 34A to 34B.

*Sepals.*—Arrangement/appearance: One per flower arranged in a spiral whorl: leaf-like. Calyx length: About 1.4 cm. Calyx width: About 8 mm. Shape: Ovate. Apex: Sharply acute. Margin: Entire. Texture: Pubescent. Color: Upper surface: 146A. Lower surface: 146B.

*Peduncles.*—Length: About 4.2 cm. Diameter: About 1.25 mm. Angle: About 25 to 30° to the stem. Strength: Flexible, but strong. Color: 144A.

*Pedicels.*—Length: Less than 1 mm. Diameter: Less than 1 mm. Color: Close to 144A.

*Reproductive organs.*—Stamens: Quantity: About four. Anther shape: Oblong. Anther length: Less than 1 mm. Anther color: Dark golden yellow. Pollen amount: None observed. Pistils: Quantity: One. Pistil length: Less than 1 mm. Stigma color: Close to 144A. Style color: 144D. Ovary color: 144A.

*Seed.*—Seed production has not been observed.

Disease resistance: Plants of the new Lantana have not been noted to be resistant to pathogens common to Lantana.

Weather tolerance: Plants of the new Lantana have been observed to be tolerant to rain and wind, tolerant to temperatures above 35° C., and hardy to at least zone 8 (USDA Hardiness Zone).

It is claimed:

1. A new and distinct cultivar of Lantana plant named 'Samson', as illustrated and described.

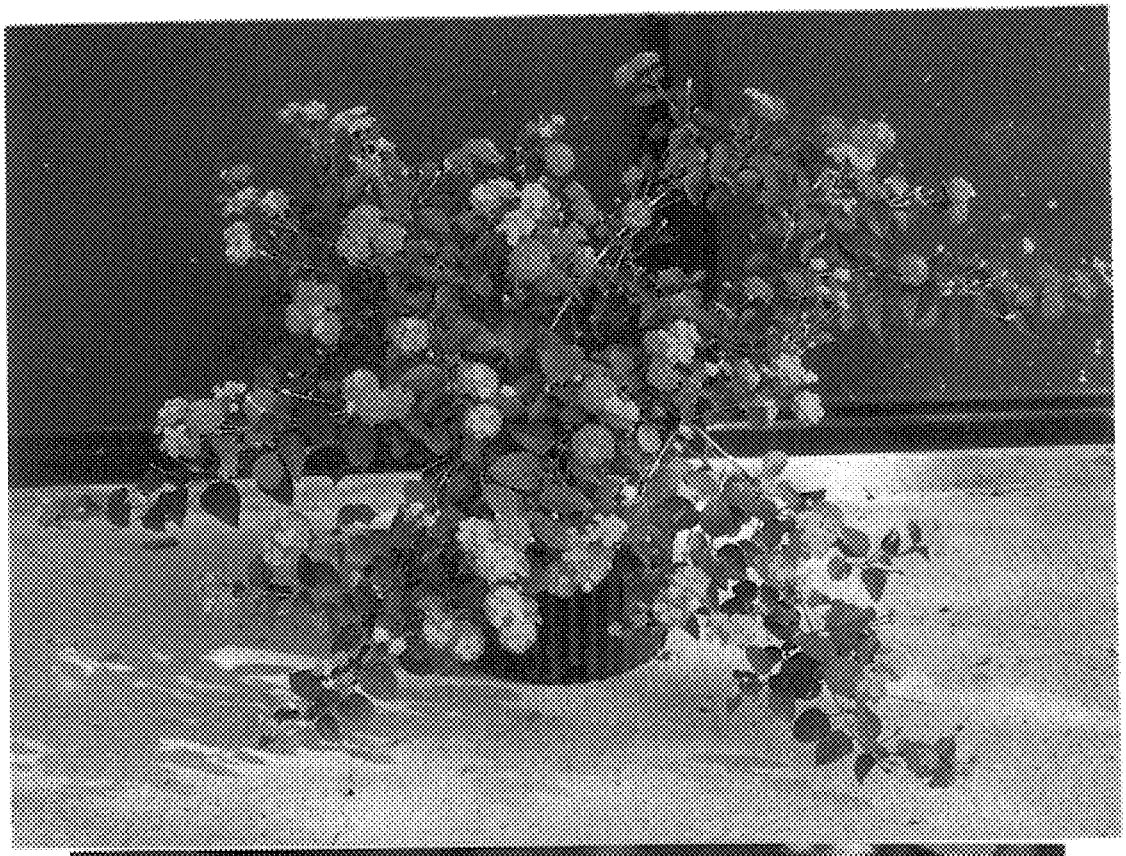
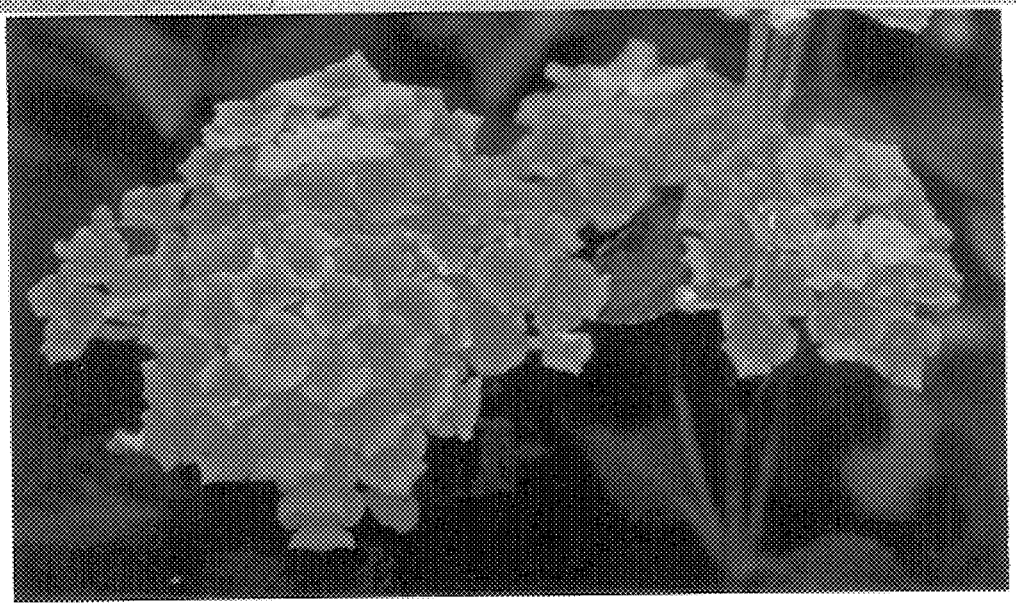

* * * * *